United States Patent
Pushpangadan et al.

(10) Patent No.: US 6,989,165 B2
(45) Date of Patent: Jan. 24, 2006

(54) SYNERGISTIC COMPOSITION FOR TREATING HYPERILIPDEMIA

(75) Inventors: Palpu Pushpangadan, Uttar Pradesh (IN); Shanta Mehrotra, Uttar Pradesh (IN); Chandana Venkateswara Rao, Uttar Pradesh (IN); Sanjeev Kumar Ojha, Uttar Pradesh (IN); Govindarajan Raghavan, Uttar Pradesh (IN); Guntupalli Madan Mohana Rao, Uttar Pradesh (IN); Sreedevi Padmavathi, Thiruvananthapuram (IN)

(73) Assignee: Council of Scientific and Industrial Research, New Delhi (IN)

( * ) Notice: Subject to any disclaimer, the term of this patent is extended or adjusted under 35 U.S.C. 154(b) by 44 days.

(21) Appl. No.: 10/815,168

(22) Filed: Mar. 31, 2004

(65) Prior Publication Data

US 2005/0136138 A1    Jun. 23, 2005

Related U.S. Application Data

(63) Continuation of application No. PCT/IB03/06106, filed on Dec. 22, 2003.

(51) Int. Cl.
*A61K 35/78* (2006.01)

(52) U.S. Cl. .................. 424/754; 424/725; 424/756; 514/824; 514/909

(58) Field of Classification Search .............. 424/725, 424/754, 756; 514/824, 909
See application file for complete search history.

(56) References Cited

U.S. PATENT DOCUMENTS

| 4,789,664 | A | * | 12/1988 | Seligson et al. | ............... 514/23 |
| 5,980,904 | A | * | 11/1999 | Leverett et al. | ............. 424/725 |
| 6,162,438 | A | * | 12/2000 | Tomer et al. | ............... 424/754 |
| 6,365,176 | B1 | * | 4/2002 | Bell et al. | .................. 424/439 |
| 2002/0136784 | A1 | * | 9/2002 | Obukowicz et al. | ........ 424/725 |
| 2004/0180104 | A1 | * | 9/2004 | Lin | ........................... 424/735 |

OTHER PUBLICATIONS

Sarg et al. Mansoura J. Pharm. Sci. 1990. vol. 6, No. 4, pp. 49-72, CAPLUS Abstract enclosed.*

* cited by examiner

*Primary Examiner*—Christopher R. Tate
(74) *Attorney, Agent, or Firm*—Merchant & Gould P.C.

(57) ABSTRACT

The present invention relates to a synergistic pharmaceutical composition useful for the treatment of hyperlipidemia, said composition comprising extracts of plant *Gentiana kurroo* of concentration ranging between 2–5 wt. %, *Murraya koenigii* of concentration ranging between 8–15 wt %, *Allium sativum* of concentration ranging between 2–4 wt %, *Zingiber officinalis* of concentration ranging between 2–5 wt %, *Amorphophallus campanulatus* of concentration ranging between 1–10%, and pharmaceutically acceptable additive(s); a process for the preparation of the said synergistic pharmaceutical composition; and also, a use of the said composition for treating hyperlipidemia, atherosclerosis, and obesity.

34 Claims, No Drawings

SYNERGISTIC COMPOSITION FOR TREATING HYPERILIPDEMIA

This application is a continuation of International Application Number PCT/IB03/06106, filed 22 Dec. 2003.

TECHNICAL FIELD

The present invention relates to a synergistic pharmaceutical composition useful for the treatment of hyperlipidemia.

BACKGROUND AND PRIOR ART REFERENCES OF THE PRESENT INVENTION

Coronary heart disease continues to be a leading cause of morbidity and mortality in developed countries. It is rapidly assuming similar trends in developing countries also[1]. It has been predicted that cardiovascular diseases will be the most important cause of mortality in India in year 2015[2]. Hyperlipidemia defined as elevation in serum levels of cholesterol and triglycerides and decrease in HDL cholesterol levels is acknowledged as a major risk factor for coronary heart disease[3]. Secondary and possible reversible forms of hyperlipidemias include diabetes mellitus, hypertension, hypothyroidism, nephritic syndrome and obstructive liver disease.

Obesity is a complex multifactorial disease that develops from the interaction between genotype and the environment. The understanding of how and why obesity occurs is incomplete, however it involves the integration of social, behavioral, cultural, physiological, metabolic and genetic factors. The presence of overweight, obesity in a patient is of medical concern for several reasons. It increases the risk for several diseases, particularly cardiovascular diseases and diabetes mellitus. According to a expert panel overweight is defined as a body mass index (BMI) of 25 to 29.3 kg/m$^2$, and obesity as BMI greater than or equal to 30 kg/m$^2$. Obesity is commonly accompanied by elevated serum triglycerides. Triglycerides rich lipoproteins may be directly atherogenic, and they are also the most common manifestation of the atherogenic lipoprotein phenotype[4]. In the presence of obesity, high serum triglycerides are commonly associated with a clustering of metabolic risk factors known as the metabolic syndrome. Thus in obese patients elevated serum triglycerides are a marker for increased cardiovascular risk.

Weight loss drugs approved by the FDA for long term use may be useful as an adjunct to diet and physical activity for patients with a BMI greater than or equal to 30 and without concomitant obesity related risk factors or diseases. The drugs used to promote weight loss have been anorexiants or appetite suppressants. These drugs work by increasing the secretion of dopamine and norepinephrine, or serotonin into the synaptic neural cleft by inhibiting the reuptake of these neurotransmitters into the neuron or by a combination of both mechanisms. Sibutramine inhibits the reuptake of norepinephrine and serotonin, but it also increases the heart rate and the blood pressure. Orlistat is not an appetite suppressant and has a different mechanism of action as it blocks about one third of fat absorption. This also causes side effects that include the decrease in absorption of fat-soluble vitamins, soft stools and anal leakage[5].

There is a great interest in weight loss drugs among the consumers. Because of the possibility of serious adverse effects, it is incumbent upon the practitioner to use the drug therapy with a lot of caution.

*Gentiana kurroo* was used in synergistic combination with other known plant parts or their extracts to form a pharmaceutically effective formulation. Accordingly studies were undertaken to develop a oral formulation containing herbal drugs along with additives for oral ingestion[6,7] to treat acute hyperlipidemia.

Details of Each of the Constituent of the Synergistic Composition of the Instant Application

*Gentiana kurroo* Family: Gentianaceae

Botanical description: A small perennial herb with a stout rhizome bearing decumbent flowering stems, each with 1–4 blue flowers, commonly found in Kashmir and north-western Himalayas, at altitudes of 5,000–11,000 ft. Leaves radical and cauline, the former oblong-lanceolate and tufted, and the latter linear and in paris united at the base in to a tube.

Phytochemistry: Catalpol, its 6'-cinnamoyl, 6-O-cinnamoyl, 6-O-vanilloyl and 6-O-feruloyl derivatives and aucubin isolated from roots and rhizomes. (Rastogi, R. P., Mehrotra, B. N. (1990–1994). Compendium of Indian Medicinal Plants. Vol. V. PID New Delhi. 387.)

Pharmacology: It is reported that the bitter principle increased the gastric secretion diminishing force of the heart beat and reduced the blood pressure. Mild laxative action was found to be due to the presence of cathartic acid. It is reported the diuretic effect of the drug.

*Murraya koenigii* Family: Rutaceae

Botanical description: A handsome aromatic, more or less decidous shrub or a small tree, up to 6 m. in height and 15–40 cm in diameter, found almost throughout India and the Andaman Islands up to an altitude of 1500 m. Bark dark brown or almost black; leaves imparpinnate: leaflets 9–25, ovate, lanceolate or somewhat rhomboid, irregularly crenate-dentate, acuminate, obtuse or acute, base usually oblique, almost glabrous above, pubscent beneath gland-dotted, strongly aromatic; flowers in terminal corymbose cymes, white, fragrant; berries sub-glucose or ellipsoid, purplish black when ripe, 2-seeded. It is commonly found in forests, often as gregarious under growth. It is much cultivated for its aromatic levesand for ornament throughout India.

Phytochemistry: Isolation and structure of pyranocarbazole alkaloid—grinimbine, mp.176°. Isolation and synthesis of murrayanine (3-formyl-1-methoxycarbazole), mp. 168°, from bark.New alkaloids—mahanimbine , mp. 94°, koenimbine, mp. 194° and koenigicine , mp. 224°—from fruits and leaves. A carbazole carboxylic acid—mukoeic acid, mp. 242°—from stem bark. Curryangine and curryanine isolated and structure of former proposed. Cyclomahanimbine and mahanimbidine isolated from leaves and their structures proposed. Girinimbine, mahanimbine and isomahanimbine isolated from leaves and roots. Structure of murrayacine isolated from leaves and roots confirmed by synthesis. Structures of mahanine, koenine, koenigine, koenidine and koenimbine isolated from leaves. Mahanimbicine and bicyclomahanimbicine isolated. Scopolin isolated from leave. Synthesis of (±)O-methylmahanine. A new carbazole—murrayacinine isolated from stern bark and its structure determined. Structure of murrayazolidine isolated from stem bark, confirmed by synthesis. Structure of curryanine (murrayazolidine) and curryagine (murrayazoline, mahanimbidine) established by synthesis. A new carbazole alkaloid—mukonine isolated and its structure established. Mukonidine isolated and characterized as 2-hydroxy-3-carbomethoxycarbazole. Structure of mahanimboline elucidated. Mahanimbinol isolated from stem wood and its structure determined. Synthesis of murrayacinine. Synthesis of koenigicinc. Structure of new hexacyclic carbazole alkaloid—isomurrayazoline elucidated. Two new carbazole alkaloids—mukoline and mukolidine isolated and their structure determined. Isolation and structure of muconicine from leaves. Mukonal isolated from stem bark and its structure determined. Stem bark afforded 3-(1,1-dimethylallyl) xanthyletin. Koenoline isolated from root bark and its structure elucidated as 1-methoxy-3-hydroxy-methylcarbazole and confirmed by synthesis. Isolation of 2-methoxy-3-methylcarbazole from seeds and its structure elucidation. Another carbazole alkaloid—2-hydroxy-3-methylcarbazole—isolated from roots. Isolation of mahanine from leaves and its 13C-NMR studied. Isolation of a carbazole alkaloid—murrayazolinol from stem bark and its structure determination. Total synthesis of mukonine, murrayanine dnd koenoline. Total seed lipids (4.4%) contained neutral lipids (85.4%), glycolipids (5.1) and phospholipids (9.5%) neutral lipids consisted of triacylglycerols (73.9), free fatty acids (10.2%) and small amount of diacylglycerols, monoacylglycerols and sterols; glycolipids contained steryl glucoside and acylated steryl glucoside; the phospholipids consisted of phosphatidylethanolamine, phosphatidylcholine, lysophosphatidylethanolamine and lysophosphatidylcholine. Isolation of two new carbazole alkaloids—isomahanine and murrayanol from fruits and their characterization by X-ray analysis; in addition, mahanimbine, murrayazolidine, girinimbine, koenimbine and mahanine isolated.

*Allium sativa* Family: Liliaceae

Botanical description: It is a small plant. The leaves are green, slender, flat and elongated. The stem is smooth and solid. The bulbs are composed of several bulhils (cloves), encased in white or pink skin of the parent bulb. The inflorescence is an umbel initially enclosed in a spathe. Garlic has long been cultivated in India as an important spice or condiment crop. It grows under much the same conditions as the onion, except that it favours a richer soil and a higher elevation.

Phytochemistry: The strong smelling juice of the bulbs contain a mixture of aliphatic mono and polysulphides. The chief constituent is allicin, diallyl disulphide oxide. The latter results from spontaneous enzymatic reduction of allin and 5-allylcystine sulphamide. Thio-glycoside, aminioacids, fatty acids, flavonols, vitamins, trace elements, volatile oils etc. have also been demonstrateds.

Pharmacology: Antibacterial and antifungal activity of garlic has been shown, by several investigators, against many common patho-genic organisms. *Staphylococcus aureus, Escheiichia coli, Candida albicans, Shigelia sonnei Salmonella typhi*. Essential oils of garlic prevented an increase in a —lipoproteins, pre— a lipoproteins occurring after cholesterol-feeding in rabbit. Fibrinolytic activity was also significantly increased. Inhibition of platelet-aggregation in vitro and in vivo has also been demonstrated with garlic. There have been several studies showing the hypoglycaemic activity of garlic and allicin in animals.

Medicinal uses: The therapeutic value of garlic in functional gastro-intestinal disorders as studied in 29 patients. A significant carminative effect, with a relief of nausea, gascolic, flatulence, belching and heaviness was observed. The effects of fried and raw garlic on blood showed an increase in fibrinolytic activity in 20 patients with ischaemic heart disease. A decrease in triglycerides and cholesterol has been observed. Garlic oil drops are put in the ears for infection and earache. Garlic is also used as an antiinfective agent topically and in other intercurrent infections.

*Zingiber officinale* Family: Zingiberaceae

Botanical description: It is a small plant. The leaves are green, slender, flat and elongated. The stem is smooth and solid. The bulbs are composed of several bulhils (cloves), encased in white or pink skin of the parent bulb. The inflorescence is an umbel initially enclosed in a spathe. Ginger has been under cultivation from times immemorial.

Medicinal uses: The therapeutic value of garlic in functional gastro-intestinal disorders was studied in 29 patients. A significant carminative effect, with a relief of nausea, gascolic, flatulence, belching and heaviness was observed. The effects of fried and raw garlic on blood showed an increase in fibrinolytic activity in 20 patients with ischaemic heart disease. A decrease in triglycerides and cholesterol has been observed. Garlic oil drops are put in the ears for infection and earache. Garlic is also used as an antiinfective agent topically and in other intercurrent infections.

Phytochemistry: The strong smelling juice of the bulbs contain a mixture of aliphatic mono and polysulphildes. The chief constituent is allicin, diallyl disulphide oxide. The latter results from spontaneous enzymatic reduction of allin and 5-allylcystine sulphamide. Thio-glycoside, aminoacids, fatty acids, flavonols, vitamins, trace elements, volatile oils etc. have also been demonstrateds.

Pharmacology: Antibacterial and antifungal activity of garlic has been shown, by several investigators, against many common patho-genic organisms. *Staphylococcus aureus, E. coli, Candida albicans, Shigelia sonnei Salmonella typhi*. Essential oils of garlic prevented an increase in a —lipoproteins, pre— a lipoproteins occurring after cholesterol-feeding in rabbits. Fibrinolytic activity was also significantly increased. Inhibition of platelet-aggregation in vitro and in vivo has also been demonstrated with garlic. There have been several studies showing the hypoglycaemic activity of garlic and allicin in animals.

*Amorphophallus campanulatus* Family: Araceae

Botanical description: A tuberous, stout, indigenous herb, 1.0–1.5 m found almost throughout India. Tubers depressed, globose or hemispherical, dark brown out side, pale dull brown, sometimes almost white, with numerous long roots; leaves solitary, tripartite, 30–90 cm broad.

Medicinal uses: The corms are irritant due to the presence of calcium oxalate. It can also be made pickles. The stems can be used as cattle feed. They are rich in nutrients and minerals. They are carminative, aperient and expectorant. The fresh ones are an acrid stimulant and expectorant and increase appetite and taste. They are applied to treat acute rheumatism. They are also used in dysentery, piles and haemorrhoids.

Phytochemistry: It is nutritious and food values compares well with other stablished. It contains proteins, fat, fiber, carbohydrates, starch, oxalic acid and minerals calcium, phosphorus, Iron and vitamin A. Besides these, glucose, galactose and xylose are also present. The presence of an active diastatic enzyme is reported. The corm contains betulinic acid, beta sitosterol, stigmasterol and beta sitosterol palmitate.

Pharmacology: The methanolic extract of the corms showed significant effect on the uterus of the guinea pig. The fermented juice of the petioles is used to cure diarrhea. The seeds are also applied externally as irritant in treating rheumatic swelling.

References

Bhatnagar, D., Current Sciene, 78: 1087 (1998)
Reddy, K. S. Wld. Hlth. StatQ., 46: 101, (1993)
Sushma Mengi, Indian J. Natural Prod., 19(1): 49 (2003)
Foster et al., J. Consult. Clinical. Physiol 65: 79–85 (1992)

Butrum et al., American J. Clin. Nutr., 48(3): 888–895 (1988)

Remington, The science and practice of pharmacy, 19$^{th}$ edition, Vol II. pp. 1635, 1995

Anonymous. Indian Pharmacopoeia. Govt of India, 1996.

OBJECTS OF THE PRESENT INVENTION

The main object of the present invention is to develop a synergistic pharmaceutical composition useful for the treatment of hyperlipidemia.

Another main object of the present invention is to develop a composition capable of reducing body weight, total serum cholesterol level, phospholipids and triglycerides.

Yet another object of the present invention is to develop a composition is useful in treating obesity, and atherosclerosis.

Still another object of the present invention is to develop a composition helps in keep slim.

Yet another main object of the invention is to develop a process for the preparation of a synergistic pharmaceutical composition useful for the treatment of hyperlipidemia.

Still object of the present invention is to provide a novel anti-hyperlipidemic herbal formulation useful as a weight loss drug in the treatment of obesity and used in atherosclerosis.

Still another objective of the present invention is to prepare herbal formulation(s) that reduces serum cholesterol, phospholipids and triglycerides.

Still another object of the present invention is to prepare herbal formulation(s) with a combination of the plants that are used in hyperlipidemia, in lowering lipid peroxidation and used as in the treatment of atherosclerosis.

SUMMARY OF THE PRESENT INVENTION

The present invention relates to a synergistic pharmaceutical composition useful for the treatment of hyperlipidemia, said composition comprising extracts of plant *Gentiana kurroo* of concentration ranging between 2–5 wt. %, *Murraya koenigii* of concentration ranging between 8–15 wt %, *Allium sativum* of concentration ranging between 2–4 wt %, *Zingiber officinalis* of concentration ranging between 2–5 wt %, *Amorphophallus campanulatus* of concentration ranging between 1–10%, and pharmaceutically acceptable additive(s); a process for the preparation of the said synergistic pharmaceutical composition; and also, a use of the said composition for treating hyperlipidemia, atherosclerosis, and obesity.

DETAILED DESCRIPTION OF THE PRESENT INVENTION

Accordingly, the present invention relates to a synergistic pharmaceutical composition useful for the treatment of hyperlipidemia, said composition comprising extracts of plant *Gentiana kurroo* of concentration ranging between 2–5 wt. %, *Murraya koenigii* of concentration ranging between 8–15 wt %, *Allium sativum* of concentration ranging between 2–4 wt %, *Zingiber officinalis* of concentration ranging between 2–5 wt %, *Amorphophallus campanulatus* of concentration ranging between 1–10%, and pharmaceutically acceptable additive(s); a process for the preparation of the said synergistic pharmaceutical composition; and also, a use of the said composition for treating hyperlipidemia, atherosclerosis, and obesity.

In an embodiment of the present invention, wherein a synergistic pharmaceutical composition useful for the treatment of hyperlipidemia, said composition comprising extracts of plant *Gentiana kurroo* of concentration ranging between 2–5 wt. %, *Murraya koenigii* of concentration ranging between 8–15 wt %, *Allium sativum* of concentration ranging between 2–4 wt %, *Zingiber officinalis* of concentration ranging between 2–5 wt %, *Amorphophallus campanulatus* of concentration ranging between 1–100%, and pharmaceutically acceptable additive(s).

In yet another embodiment of the present invention, wherein the additives are selected from a group comprising binders, diluents, and lubricants.

In still another embodiment of the present invention, wherein the binder is selected from a group comprising starch, starch paste, gum acacia, and carboxy methylcellulose.

In still another embodiment of the present invention, wherein the diluent is lactose.

In still another embodiment of the present invention, wherein the lubricant is selected from a group comprising starch, and lactose.

In still another embodiment of the present invention, wherein the composition is administered orally.

In still another embodiment of the present invention, wherein the extracts are obtained from plant parts selected from a group comprising leaf, rhizome, and aerial parts.

In still another embodiment of the present invention, wherein the extract of plant *Gentiana Kurroo* is a root extract.

In still another embodiment of the present invention, wherein the composition is in lyophilized form.

In still another embodiment of the present invention, wherein the composition reduces body weight, total serum cholesterol level, phospholipids and triglycerides.

In still another embodiment of the present invention, wherein the composition is useful in treating obesity, and atherosclerosis.

In still another embodiment of the present invention, wherein the composition helps in keep slim.

In still another embodiment of the present invention, wherein a process for the preparation of a synergistic pharmaceutical composition useful for the treatment of hyperlipidemia, said composition comprising extracts of plant *Gentiana kurroo* of concentration ranging between 2–5 wt. %, *Murraya koenigii* of concentration ranging between 8–15 wt %, *Allium sativum* of concentration ranging between 2–4 wt %, *Zingiber officinalis* of concentration ranging between 2–5 wt %, *Amorphophallus campanulatus* of concentration ranging between 1–10%, and pharmaceutically acceptable additive(s), said process comprising steps of:

drying leaves, rhizome and/or aerial parts of the aforementioned plants in shade,
  powdering the dried plant material to a coarse powder,
  extracting the powdered dried plant material with 35 to 55% alcohol in the ratio of 1:7 to 1:17 at room temperature for time duration ranging between 3–8 days,
  concentrating the extract at under reduced pressure at temperature ranging between 35–65° C.,
  lyophilizing the concentrated extract for complete removal of solvent, and
  blending the lyophilized extract with additives to obtain the composition.

In still another embodiment of the present invention, wherein the alcohol is ethanol.

In still another embodiment of the present invention, wherein the room temperature is ranging between 25 to 35° C.

In still another embodiment of the present invention, wherein the additives constitutes the remaining wt % of the composition after addition of herbal extracts.

In still another embodiment of the present invention, wherein the extract of plant *Gentiana kurroo* is a root extract.

In still another embodiment of the present invention, wherein the additives are selected from a group comprising binders, diluents, and lubricants.

In still another embodiment of the present invention, wherein the binder is selected from a group comprising starch, starch paste, gum acacia, and carboxy methylcellulose.

In still another embodiment of the present invention, wherein the diluent is lactose.

In still another embodiment of the present invention, wherein the lubricant is selected from a group comprising starch, and lactose.

In still another embodiment of the present invention, wherein use of a synergistic pharmaceutical composition comprising extracts of plant *Gentiana kurroo* of concentration ranging between 2–5 wt. %, *Murraya koenigii* of concentration ranging between 8–15 wt %, *Allium sativum* of concentration ranging between 2–4 wt %, *Zingiber officinalis* of concentration ranging between 2–5 wt %, *Amorphophallus campanulatus* of concentration ranging between 1–10 %, and pharmaceutically acceptable additive(s) to a subject in a need thereof for treating hyperlipidemia, by administering pharmaceutically effective amount of the said composition.

In still another embodiment of the present invention, wherein the extract of plant *Gentiana kurroo* is a root extract.

In still another embodiment of the present invention, wherein the additives are selected from a group comprising binders, diluents, and lubricants.

In still another embodiment of the present invention, wherein the binder is selected from a group comprising starch, starch paste, gum acacia, and carboxy methylcellulose.

In still another embodiment of the present invention, wherein the diluent is lactose.

In still another embodiment of the present invention, wherein the lubricant is selected from a group comprising starch, and lactose.

In still another embodiment of the present invention, wherein the method decreases hyperlipidemia by about 20–30%.

In still another embodiment of the present invention, wherein the composition is useful in the treatment of atherosclerosis.

In still another embodiment of the present invention, wherein the composition is useful in the treatment of obesity.

In still another embodiment of the present invention, wherein the method reduces body weight, total serum cholesterol level, phospholipids and triglycerides by about 18–25%.

In still another embodiment of the present invention, wherein the method helps in maintaining slimness.

In still another embodiment of the present invention, wherein the subject is an animal.

In still another embodiment of the present invention, wherein the subject is a human.

Accordingly the present invention provides a herbal formulation useful in the treatment of hyperlipidemia. The herbal formulation comprising of *Gentiana kurroo* as the active ingredient. Along with this plants, others like *Murraya koenigii, Allium sativum, Zingiber officinale Amorphophallus campanulatus* are added which are used in intestinal discomforts and as an galactogogue together with conventional additives.

The invention provides a novel herbal synergistic formulation for treatment of hyperlipidemia, obesity, atherosclerosis and used in maintaining slimness. Formulation(s) comprises of plant parts or plant extracts together with the conventional additives to form the oral dosage forms, which include tablets, capsules and powders ready for suspension. *Gentiana kurroo* along with this plant used with *Murraya koenigii, Allium sativum, Zingiber officinale* and *Amorphophallus campanulatus* are added which are used for lowering serum cholesterol.

Accordingly, the present invention provides a novel antihyperlipidemic herbal synergistic formulation useful for the treatment of obesity, atherosclerosis, said formulation comprising:

a) 50% aqueous alcoholic extracts of the plants comprising *Gentiana kurroo* 2–5 wt. %, *Murraya koenigii* 8–15 wt. %, *Allium sativum* 2–4 wt. %, *Zingiber officinale* 2–5 wt. % and *Amorphophallus campanulatus* 1–10% in an oral dosage form selected from a group consisting of a tablet, a capsule, a powder and a liquid.

The novelty of the present investigation is (1) herbal formulation for the treatment of obesity (2) the herbal formulation acts as and antihyperlipidemic agent (3) the herbal formulation is useful in treating atherosclerosis.

In another embodiment, the composition as claimed in claim 1 wherein the additives are selected from powdered plant parts or lyophilized extracts of plants *Murraya koenigii, Allium sativum, Zingiber officinale, Amorphophallus campanulatus.*

In another embodiment, herbal formulation(s) as claimed in claim 1 & 2 wherein the extracts of the plants are mixed in the ratio *Gentiana kurroo* 2–5 wt. %, *Murraya koenigii* 8–15 wt. %, *Allium sativum* 2–4 wt. %, *Zingiber officinale* 2–5 wt. % and *Amorphophallus campanulatus* 1–10 wt. % along with conventional additives to form an oral dosage form.

In yet another embodiment, herbal formulation(s) as claimed in claim 1 wherein the said composition treats hyperlipidemia.

In yet another embodiment, herbal formulation(s) as claimed in claim 1 wherein the said composition lowers body weight in obesity conditions.

In still another embodiment, herbal formulation(s) as claimed in claim 1 wherein the said composition treats hyperlipidemia and lowers total serum cholesterol level.

In another embodiment, herbal formulation(s) as claimed in claim 1 wherein the said composition treats hyperlipidemia and lowers phospholipids.

In another embodiment, herbal formulation(s) as claimed in claim 1 wherein the said composition treats hyperlipidemia and maintains the triglyceride levels.

In another embodiment, herbal formulation(s) as claimed in claim 1 wherein the formulation cures atherosclerosis.

In yet another embodiment, herbal formulation(s) as claimed in claim 1 wherein said composition in an oral dosage form selected from a group consisting of a tablet, a capsule, a powder and a liquid.

In yet another embodiment, herbal formulation(s) as claimed in claim 1 wherein the extracts of plants are 50% aqueous alcoholic extract.

In yet another embodiment, herbal formulation(s) as claimed in claim 1 wherein the alcohol used is ethanol.

In another embodiment, herbal formulation(s) as claimed in claim 1 wherein the said composition comprises about 12–29% wt of the total formulation.

In still another embodiment, herbal formulation(s) as claimed in claim 1 wherein the extract of *Gentiana kurroo* is a root extract.

In yet another embodiment, herbal formulation(s) as claimed in claim 1 wherein the plant extracts are obtained: from plant parts selected from leaf, rhizome and aerial parts.

In yet another embodiment, herbal formulation(s) as claimed in claim 1 wherein the binders used are starch, starch paste, gum acacia and carboxy methyl cellulose.

In yet another embodiment, herbal formulation(s) as claimed in claim 1 wherein the diluents used are lactose.

In another embodiment, herbal formulation(s) as claimed in claim 1 wherein the lubricants used are from starch and lactose.

In still another embodiment, herbal formulation(s) as claimed in claim 1 wherein the formulation is used in treating intestinal discomforts and acts as a antimicrobial agent.

In yet another embodiment, A method of preparing a herbal formulation as claimed in claim 1 wherein the said method comprising:
  a. Obtaining the part of medicinal plants from a group comprising leaves, rhizome and aerial parts.
  b. Drying the plant material in shade.
  c. Powdering the dried plant material to a coarse powder.
  d. Extracting the powdered dried plant material with (40–50% aqueous ethanol) at 25–35° C.
  e. Extracting the plant material with the Aqueous alcohol in the ratio of 1:8 to 1:15 for 4–7 days
  f. Concentrating the obtained extract at under reduced pressure at 40–60° C.
  g. Lyophilising the concentrated extract for complete removal of solvent.

In still another embodiment, herbal formulation(s) as claimed in claim 1 wherein the said composition dose dependently lowers body weight from 236.9±5.1 g in control to 181.6±4.2 g after 7–15 days in rats.

In yet another embodiment, herbal formulation(s) as claimed in claim 1 wherein the formulation at a higher doses or dose of 400 mg/kg reduced total cholesterol from 87.6±3.25 mg/dl in control to 77.6±2.32 mg/dl after 7–15 days in rat serum.

In another embodiment, herbal formulation(s) as claimed in claim 1 wherein the formulation at a dose or in dose of 400 mg/kg maintains triglyceride levels of that of the normal conditions.

In yet another embodiment, herbal formulation(s) as claimed in claim 1 wherein the formulation at a dose of 400 mg/kg reduced phospholipids from 126.5±4.67 mg/dl in control to 103.1±3.21 mg/dl after 7–15 days in rat serum.

As a result of intensive study conducted by the inventors with the aim of achieving aforementioned objectives, new formulations for oral ingestion were developed employing herbal drugs, which are from natural origin, incorporating them into binders and diluents to form oral dosage forms.

Accordingly, the present investigation deals with the oral dosage form formulation(s). Each formulation has been described in detail giving the formula of the ingredients along with the method of preparation.

The first step in the preparation of these formulations involves a process for making, the plant material suitable for formulating into a tablet/capsule. The specified portion of the plant is collected and dried under shade at room temperature (25–35° C.) for 72 hours or until the material gets dried. The material is then powdered into a fine powdered. A specified amount of the powdered material is then extracted exhaustively with 50% aqueous alcohol at room temperature (25–35° C.). Extraction was carried out in a closed container immersing specified amount of the plant material in specified solvent (1:8–1:15 ratio) for 4–7 days. At the end of this stage, solvent is decanted and filtered if necessary to make it free from plant debris. The solvent is then concentrated by evaporating under vacuum at less than 40–60° C. The concentrate is then freeze dried to obtain final product in powder form. The final product is then made into oral dosage form by using it as an ingredient for making tablets and capsules. Suitable binders like starch and diluents like lactose are added to make up the formulation.

The instant invention is further elaborated with the help of following examples; however, the examples should not be construed to limit the scope of the invention.

EXAMPLE 1

| Formulation - 1 | |
| --- | --- |
| *Gentiana kurroo* | 3 wt. % |
| *Murraya koenigii* | 10 wt. % |
| *Allium sativum* | 3 wt. % |
| *Zingiber officinale* | 4 wt. % |
| *Amorphophallus campanulatus* | 6 wt. % |
| Starch paste | 15 wt. % |
| Talc | 1 wt. % |
| Lactose | q.s. to make 100% |

*Gentiana kurroo, Murraya koenigii, Allium sativum* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16-mesh screen. Talc is added to the dried granules and then they are punched in the tablet-punching machine to form uniform tablets.

The formulation is useful for the treatment of hyperlipidemia

EXAMPLE 2

| Formulation - 2 | |
| --- | --- |
| *Murraya koenigii* | 12 wt. % |
| *Allium sativum* | 2 wt. % |
| *Zingiber officinale* | 3 wt. % |

-continued

| Formulation - 2 | |
|---|---|
| *Amorphophallus campanulatus* | 8 wt. % |
| Lactose | q.s to make 100% |

*Murraya koenigii*, *Allium sativum* and *Zingiber officinale* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. The weighed quantities of the plant extracts as mentioned are mixed with the diluent lactose and then are filled in hard gelatin capsules and are dispensed.

The formulation is useful for reducing body weight and in the treatment of atherosclerosis Results:

TABLE 1

Effect of hypolipidemic formulation (F1) on body weight (g) in rats

| Experimental groups | (mg/kg) | Body weight (g) 0 day | 15 days |
|---|---|---|---|
| Control | — | 223.8 ± 3.1 | 236.9 ± 5.1 |
| Formulation | 100 | 230.1 ± 3.6 | 211.3 ± 4.7* |
| Formulation | 200 | 228.5 ± 3.3 | 197.5 ± 4.8** |
| Formulation | 400 | 232.6 ± 3.7 | 181.6 ± 4.2*** |
| Vanadate | 0.8 | 227.5 ± 2.9 | 201.1 ± 3.9* |

Values are mean ± S.E.M. for six or eight rats.
P: <0.05
**<0.01 and
***<0.001 compared to respective control group.
NOTE:
No mortality was found in any of the treated group.
No gross abnormality in behavior was observed in the animal exposed with hypolipidemic formulation
The F1 formulation contains the highly potent plant called *Gentiana kurroo* with some other plant extracts viz. *Murrya koenigii*, *Allium sativum*, *Zingiber officinale* and *Amorphophallus campanulatus*. The results showed a significant decrease in the bodyweight with that of control. The positive control ie vanadate showed the less significant ($P < 0.05$) than that of formulation F1 ($P < 0.05$ to $P < 0.001$). Hence formulation is highly effective than that of the known drug vanadate.

TABLE 2

Effect of hypolipidemic formulation (F2) containing only the *Murrya koenigii*, *Allium sativum*, *Zingiber officinale* and *Amorphophallus campanulatus* without active plant on body weight (g) in rats

| Experimental groups | (mg/kg) | Body weight (g) 0 day | 15 days |
|---|---|---|---|
| Control | — | 218.9 ± 4.3 | 231.5 ± 4.8 |
| F2 | 100 | 221.5 ± 4.5 | 220.2 ± 5.6 |
| F2 | 200 | 223.2 ± 4.1 | 210.5 ± 3.2* |
| F2 | 400 | 220.1 ± 3.9 | 198.2 ± 2.8* |

Values are mean ± S.E.M. for six or eight rats.
P: *<0.01 compared to control.
NOTE:
No mortality was found in any of the treated group.
No gross abnormality in behavior was observed in the animal exposed with hypolipidemic formulation.
F2 contains *Murrya koenigii*, *Allium sativum* and *Zingiber officinale*, and *Amorphophallus campanulatus* extract.

The result of table 2 showed that there is no significant different in the lower dose range of 100–400 mg/kg. But at the dose level of 400 mg/kg showed the significance ($P<0.05$) than that of the formulation (F1) of table 1, so the F1 is highly effective and showed a synergistic effect represented the slimming effect.

TABLE 3

Effect of hypolipidemic herbal formulation (F1) on lipid levels in rat serum

| Treatment | (mg/kg) | Total Cholestrol (mg/dl) | Phospholipids (mg/dl) | Triglycerides (mg/dl) |
|---|---|---|---|---|
| Control | — | 87.6 ± 3.25 | 126.5 ± 4.67 | 67.80 ± 3.51 |
| F1 | 100 | 82.5 ± 2.66 | 118.9 ± 5.10* | 63.51 ± 3.90 |
| F1 | 200 | 77.6 ± 2.32** | 103.1 ± 3.21** | 61.21 ± 3.28 |
| F1 | 400 | 68.9 ± 2.52 | 98.2 ± 2.81*** | 52.30 ± 3.10* |

Values are mean ± S.E.M. for six or eight rats.
P:
*<0.05,
**<0.01 and
***<0.001 compared to respective control group.
NOTE:
No mortality was found in any of the treated group.
No gross abnormality in behavior was observed in the animal exposed with hypolipidemic formulation
The F1 formulation contains *Gentiana kurroo* along with *Murrya koenigii*, *Allium sativum*, *Zingiber officinale* and *Amorphophallus campanulatus* extract.

The table-3 represents the level of phospholipids, which decreased, significantly with the dose of 200–400 mg/kg body weight of rat. The total cholesterol level at the dose of 400 mg.kg reduced significantly and there is a significant change in triglyceride level in rat serum at higher dose and therefore it represents the use of the formulation as an antihyperlipidemic, atherosclerosis, obesity and acts as a slimming composition/drug.

TABLE 4

Effect of hypolipidemic herbal formulation (F2) contains *Murrya koenigii*, *Allium sativum*, *Zingiber officinale* and *Amorphophallus campanulatus* on lipid levels in rat serum.

| Treatment | | Total Cholestrol (mg/dl) | Phospholipids (mg/dl) | Triglycerides (mg/dl) |
|---|---|---|---|---|
| Control | — | 87.5 ± 3.23 | 113.6 ± 4.59 | 68.2 ± 3.56 |
| F2 | 200 | 85.3 ± 3.12 | 101.2 ± 2.32 | 52.3 ± 4.52 |

Values are mean ± S.E.M. for six or eight rats.
NOTE:
No mortality was found in any of the treated group.
No gross abnormality in behavior was observed in the animal exposed with hypolipidemic formulation
F2 contains *Murrya koenigii*, *Allium sativum* and *Zingiber officinale*, and *Amorphophallus campanulatus* extract.

The level of total cholestrol, phopholipids and triglycerides were not significantly changed in rat serum at a dose of 200 mg/kg body weight in rat. While the formulation F1 of table 3 represents better results and used accordingly with the object of our investigation.

TABLE 5

Organ weight of rats in sub-acute toxicity of hypolipidemic formulation (F1)

| Treatment | | Lung | Heart | Liver | Spleen | Adrenal | Kidney | ovary |
|---|---|---|---|---|---|---|---|---|
| | | Organ weight (g/100 g body weight) | | | | | | |
| Control | — | 0.43 ± 0.01 | 0.40 ± 0.01 | 3.10 ± 0.01 | 0.25 ± 0.01 | 0.01 ± 0.00 | 0.44 ± 0.03 | 0.70 ± 0.01 |
| F1 | 400 | 0.42 ± 0.01 | 0.39 ± 0.01 | 2.98 ± 0.01 | 0.26 ± 0.01 | 0.01 ± 0.00 | 0.43 ± 0.02 | 0.69 ± 0.01 |
| F1 | 800 | 0.41 ± 0.01 | 0.40 ± 0.01 | 2.91 ± 0.01 | 0.27 ± 0.01 | 0.01 ± 0.00 | 0.41 ± 0.01 | 0.61 ± 0.01 |

NOTE:
No mortality was found in any of the treated group.
No gross abnormality in behavior was observed in the animal exposed with hypolipidemic formulation
The F1 formulation contains the highly potent plant called *Gentiana kurroo* with some other plant extracts viz. *Murrya koenigii*, *Allium sativum*, *Zingiber officinale* and *Amorphophallus campanulatus*.

The result of table 5 represents the sub-acute toxicity results which there is no change or effect on the normal functioning on the body weight of the vital organs viz. lung, heart, liver, spleen, adrenal, kidney and ovary in rats. Therefore the F1 formulation is safe and non-toxic.

Advantages of the Present Invention

1. Reduces body weight.
2. Useful in the treatment of hyperlipidemia.
3. Used to lower serum cholesterol, phospholipids and triglycerides.
4. Useful in curing atherosclerosis.

What is claimed is:

1. A synergistic pharmaceutical composition useful for the treatment of hyperlipidemia, said composition comprising extracts of the plants *Gentiana kurroo* at a concentration ranging between 2–5 wt %, *Murraya koenigii* at a concentration ranging between 8–15 wt %, *Allium sativum* at a concentration ranging between 2–4 wt %, *Zingiber officinalis* at a concentration ranging between 2–5 wt %, *Amorphophallus campanulatus* at a concentration ranging between 1–10 wt %, and one or more pharmaceutically acceptable additive(s).

2. The composition as claimed in claim 1, wherein the additives are selected from a group comprising binders, diluents, and lubricants.

3. The composition as claimed in claim 2, wherein the binder is selected from a group comprising starch, starch paste, gum acacia, and carboxy methylcellulose.

4. The composition as claimed in claim 2, wherein the diluent is lactose.

5. The composition as claimed in claim 2, wherein the lubricant is selected from a group comprising starch, and lactose.

6. The composition as claimed in claim 1, wherein the composition is administered orally.

7. The composition as claimed in claim 1, wherein the extracts are obtained from plant parts selected from a group comprising leaf, rhizome, and aerial parts.

8. The composition as claimed in claim 1, wherein the extract of plant *Gentiana Kurroo* is a root extract.

9. The composition as claimed in claim 1, wherein the composition is in lyophilized form.

10. The composition as claimed in claim 1, wherein the composition reduces body weight, total serum cholesterol level, phospholipids and triglycerides.

11. The composition as claimed in claim 1, wherein the composition is useful in treating obesity, and atherosclerosis.

12. The composition as claimed in claim 1, wherein the composition helps in keep slim.

13. A process for the preparation of a synergistic pharmaceutical composition useful for the treatment of hyperlipidemia, said composition comprising extracts of the plants *Gentiana kurroo* at a concentration ranging between 2–5 wt %, *Murraya koenigii* at a concentration ranging between 8–15 wt %, *Allium sativum* at a concentration ranging between 2–4 wt %, *Zingiber officinalis* at a concentration ranging between 2–5 wt %, *Amorphophallus campanulatus* at a concentration ranging between 1–10 wt %, and one or more pharmaceutically acceptable additive, said process comprising steps of:

a. drying leaves, rhizome and/or aerial parts of the aforementioned plants in shade,
b. powdering the dried plant material to a coarse powder,
c. extracting the powdered dried plant material with 35 to 55% alcohol in the ratio of 1:7 to 1:17 at room temperature for time duration ranging between 3–8 days,
d. concentrating the extract at under reduced pressure at temperature ranging between 35–65° C.,
e. lyophilizing the concentrated extract for complete removal of solvent, and
f. blending the lyophilized extract with additives to obtain the composition.

14. The process as claimed in claim 13, wherein the alcohol is ethanol.

15. The process as claimed in claim 13, wherein the room temperature is ranging between 25 to 35° C.

16. The process as claimed in claim 13, wherein the additives constitutes the remaining wt % of the composition after addition of herbal extracts.

17. The process as claimed in claim 13, wherein the extract of plant *Gentiana kurroo* is a root extract.

18. The process as claimed in claim 13, wherein the additives are selected from a group comprising binders, diluents, and lubricants.

19. The process as claimed in claim 18, wherein the binder is selected from a group comprising starch, starch paste, gum acacia, and carboxy methylcellulose.

20. The process as claimed in claim 18, wherein the diluent is lactose.

21. The process as claimed in claim 18, wherein the lubricant is selected from a group comprising starch, and lactose.

22. A method for treating hyperlipidemia comprising administering to a subject in need thereof a synergistic pharmaceutical composition comprising extracts of the plants *Gentiana kurroo* at a concentration ranging between 2–5 wt %, *Murraya koenigii* at a concentration ranging between 8–15wt %, *Allium sativum* at a concentration ranging between 2–4 wt %, *Zingiber officinalis* at a concentration ranging between 2–5 wt %, *Amorphophallus campanulatus* at a concentration ranging between 1–10 wt %, and one or more pharmaceutically acceptable additive.

23. The method of claim 22, wherein the extract of plant *Gentiana kurroo* is a root extract.

24. The method of claim 22, wherein the additives are selected from a group comprising binders, diluents, and lubricants.

25. The method of claim 24, wherein the binder is selected from a group comprising starch, starch paste, gum acacia, and carboxy methylcellulose.

26. The method of claim 24, wherein the diluent is lactose.

27. The method of claim 24, wherein the lubricant is selected from a group comprising starch, and lactose.

28. The method of claim 22, wherein the method decreases hyperlipidemia by about 20–30%.

29. A method for treating atherosclerosis, comprising administering to a subject in need thereof the composition of claim 1.

30. A method for treating obesity comprising administering to a subject in need thereof the composition of claim 1.

31. The method of claim 22, wherein the method reduces body weight, total serum cholesterol level, phospholipids and triglycerides by about 18–25%.

32. The method of claim 22, wherein the method helps in maintaining slimness.

33. The method of claim 22, wherein the subject is an animal.

34. The method of claim 22, wherein the subject is a human.

* * * * *